United States Patent
Shahriar

(10) Patent No.: US 10,537,256 B2
(45) Date of Patent: Jan. 21, 2020

(54) HEALTH AND FITNESS MONITOR FOR DETERMINING A MINIMUM HEART RATE

(71) Applicant: Nokia Technologies Oy, Espoo (FI)

(72) Inventor: Muneem Shahriar, Sunnyvale, CA (US)

(73) Assignee: Nokia Technologies Oy, Espoo (FI)

(*) Notice: Subject to any disclaimer, the term of this patent is extended or adjusted under 35 U.S.C. 154(b) by 430 days.

(21) Appl. No.: 15/374,138

(22) Filed: Dec. 9, 2016

(65) Prior Publication Data

US 2018/0160920 A1 Jun. 14, 2018

(51) Int. Cl.
*A61B 5/02* (2006.01)
*A61B 5/024* (2006.01)
*A61B 5/00* (2006.01)

(52) U.S. Cl.
CPC ...... *A61B 5/02405* (2013.01); *A61B 5/02438* (2013.01); *A61B 5/725* (2013.01); *A61B 5/0002* (2013.01); *A61B 5/4806* (2013.01); *A61B 5/7221* (2013.01); *A61B 5/7267* (2013.01)

(58) Field of Classification Search
CPC . A61B 5/02405; A61B 5/725; A61B 5/02438; A61B 5/7267; A61B 5/7221; A61B 5/0002; A61B 5/4806
See application file for complete search history.

(56) References Cited

U.S. PATENT DOCUMENTS

| 4,259,966 | A | 4/1981 | Cannon et al. | |
| 2007/0113725 | A1* | 5/2007 | Oliver | A61B 5/02438 84/612 |
| 2010/0268103 | A1 | 10/2010 | McNamara et al. | |
| 2014/0066782 | A1 | 3/2014 | Addison et al. | |
| 2014/0073486 | A1* | 3/2014 | Ahmed | A61B 5/02405 482/9 |
| 2015/0005654 | A1 | 1/2015 | Hopenfeld | |
| 2016/0256058 | A1 | 9/2016 | Pham et al. | |
| 2016/0361011 | A1* | 12/2016 | Fung | A61B 5/4809 |
| 2017/0031449 | A1* | 2/2017 | Karsten | G06F 19/3418 |

FOREIGN PATENT DOCUMENTS

| EP | 2893878 A1 | 7/2015 |
| WO | WO-2015107891 A1 | 7/2015 |

* cited by examiner

*Primary Examiner* — Mallika D Fairchild
(74) *Attorney, Agent, or Firm* — Mintz Levin Cohn Ferris Glovsky and Popeo, P.C.

(57) ABSTRACT

Methods and apparatus, including computer program products, are provided for analyzing heart rate data for a fitness or health device. In some example embodiments, there may be provided an apparatus that includes at least one processor and at least one memory including program code which when executed configures the apparatus to at least: receive, from at least one heart rate sensor, a heart rate data set collected from a subject over at least one session; filter the heart rate data set to remove at least one heart rate value failing to satisfy a predetermined duration threshold; determine a minimum heart rate value from the filtered heart rate data; and provide the determined minimum heart rate. Related systems, methods, and articles of manufacture are also described.

17 Claims, 12 Drawing Sheets

HEALTH AND FITNESS MONITOR FOR DETERMINING A MINIMUM HEART RATE

FIELD

The subject matter described herein relates to data analytics and, in particular, heart rate measurement processing.

BACKGROUND

Numerous devices today can be used to measure heart rate. Indeed, wearers of some of these devices monitor heart rate for fitness or health reasons. For example, runners often track heart rate to maximize the effects of running by training at a certain heart rate. However, some of these devices provide heart rate measurements that are inaccurate and not repeatable.

SUMMARY

Methods and apparatus, including computer program products, are provided determining a minimum heart rate.

In some example embodiments, there may be provided an apparatus that includes at least one processor and at least one memory including program code which when executed configures the apparatus to at least: receive, from at least one heart rate sensor, a heart rate data set collected from a subject over at least one session; filter the heart rate data set to remove at least one heart rate value failing to satisfy a predetermined duration threshold; determine a minimum heart rate value from the filtered heart rate data; and provide the determined minimum heart rate.

In some variations, one or more of the features disclosed herein including the following features can optionally be included in any feasible combination. The heart rate data set may include heart rate data associated with a sleep session of the subject. The apparatus may filter the heart rate data set by at least applying an adaptive threshold to the heart rate data set. The apparatus may filter the heart rate data set by at least applying an adaptive threshold to filter a histogram of the heart rate data set. The filter may remove the at least one heart rate data value above the adaptive threshold. The apparatus may be further configured to at least segment the heart rate data into a plurality of groups. The apparatus may be further configured to at least remove a group if the group is less than the predetermined duration threshold. The apparatus may be further configured to at least determine a group heart rate value for each of the plurality of groups. The determined minimum heart rate value may correspond to a candidate minimum heart rate value determined from the plurality of group heart rate values. The determined minimum heart rate may correspond to a final minimum heart rate value determined from a plurality candidate minimum heart rate values corresponding to a plurality of sessions. The final minimum heart rate value may be determined as a minimum having a threshold amount of repeat values within a histogram. The heart rate data set may include awake state heart rate data. The apparatus may be further configured to at least estimate, from the awake state heart rate data, sleep state heart rate data. The apparatus may be further configured to at least determine the minimum heart rate based at least in part on the sleep state heart rate data estimated from the awake state heart rate data. The apparatus may include a server coupled to the internet. The apparatus may include a user equipment. The at least one heart rate sensor may wirelessly couple to the apparatus. The determined minimum heart rate may be provided in response to a query for the minimum heart rate.

The above-noted aspects and features may be implemented in systems, apparatus, methods, and/or articles depending on the desired configuration. The details of one or more variations of the subject matter described herein are set forth in the accompanying drawings and the description below. Features and advantages of the subject matter described herein will be apparent from the description and drawings, and from the claims.

Figure 1:
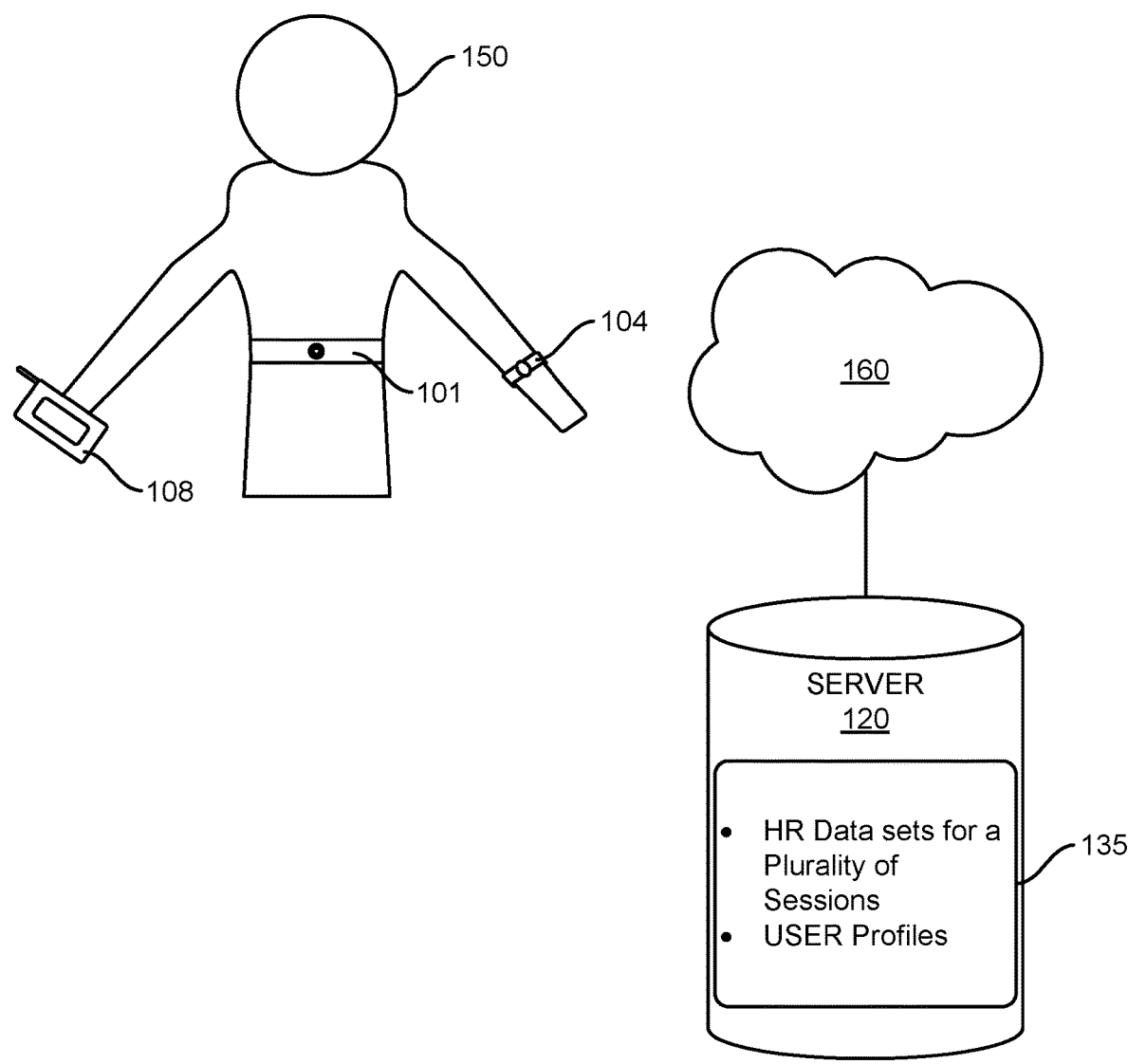
FIG. 1 depicts an example of a system, in accordance with some example embodiments.

Like labels are used to refer to same or similar items in the drawings.

DETAILED DESCRIPTION

A subject's resting heart rate (RHR) may be the heart rate for the subject while at rest, such as when the subject is in a supine position. For example, when an individual initially wakes up, the measured heart rate may represent the subject's RHR. Some devices use RHR and/or use RHR to derive other health and/or fitness parameters. However, RHR measurements may vary substantially. For example, RHR measurements from one day to the next can vary substantially due to for example various factors, such as quality of sleep on any given night, short-term sickness, ambient conditions, and/or the like. Although using the average RHR can seem like a reasonable choice, the variability of RHR may indicate that it is not a stable, baseline measurement of a subject's heart rate even if averaged. As such, RHR may not be an optimum choice to base other health and/or fitness parameters.

In some example embodiments, there is provided a way to determine a minimum heart rate (MHR) for a given subject.

The determined MI-1R may, in some example embodiments, be used to derive other parameters related to the subject's health and/or fitness, such as desired target heart rates for training zones, VO2 max, calorie burn, deep and light sleep estimation, estimating stressful periods, and/or the like. MHR may refer to a heart rate at which the parasympathetic nervous system (PNS) may be considered most dominant as PNS inhibits heart rate. Physiologically, MHR may be considered a low, or lowest, heart rate measurement that an individual may attain. Often, the MHR can be attained while sleeping. In some example embodiments, the MHR may be determined over a predetermined period of time, such as over one evening of heart rate data, over one day of heart rate data, over two days of heart rate data, over three days of heart rate data, and/or other durations such as hours, days, weeks, months, or years.

MHR may be considered a more stable, baseline heartrate measurement, when compared to RHR. For example, MHR does not usually change from day to day as can RHR. Although MHR can change over time, the MHR change may be more gradual, when compared to RHR. For example, MHR may vary slowly over a longer period of time, such as weeks, months, or years due to lifestyle changes or for other reasons. Although MHR is a more stable, baseline measurement when compared to RHR, MHR may be considered more difficult to determine as MHR may require a collection of measurements, such as time-series data, collected over a longer period of time. For example, heart rate data may represent heart rate in beats per unit of time, and, in some implementations, each the heart rate data value may have a corresponding time stamp indicating when the heat rate was determined/measured. However, in some implementations, the heart rate measurement is collected at predetermined times (or intervals), so a time stamp may not be needed as the timing can be implicit in the measurement.

FIG. 1 depicts an example of a system 100, in accordance with some example embodiments. The system 100 may include at least one sensor 101 configured to at least gather data to enable a determination of a minimum heart rate (MHR) for a subject 150.

The MHR may be determined from at least data representative of heart rate collected by at least one sensor 101 configured to measure or gather heart rate data. The at least one sensor 101 may take a variety of forms. For example, the sensor 101 may comprise a chest strap including circuitry configured to detect the heart beasts (e.g., electrically) and generate a signal (e.g., an electrocardiogram, EKG/ECG, signal or data values representative of the heart beats and time stamps) to enable a determination of a subject's heart rate, although other types of sensors may be used as well including wrist-based heart rate monitors, optical heart rate monitors (e.g., infrared-light based devices coupled to a finger, such as a pulse oximeter providing a photoplethysmogram), and/or any other device which can generate and/or provide data from which heart rate can be determined. Alternatively or additionally, the sensor 101 may comprise an electrocardiograph (ECG) and/or ECG lead(s) coupled to a subject's chest. Furthermore, the sensor 101 may provide the data as a discrete or continuous signal or time series data over a period of time such as seconds, minutes, hours, days, weeks, and/or months.

Alternatively or additionally, the sensor 101 may, via a wired or wireless connection, couple to a receiver, such as a wearable receiver 104 (e.g., a wrist-based receiver, smart watch, and/or the like), smart phone 108, tablet, computer, and/or the like. Moreover, the wearable receiver 104 and/or smart phone 108 may also be configured as a sensor to measure and/or gather data, which can be used to determine MHR or other parameters as well.

Alternatively or additionally, the sensor 101 may couple to a server 120, either directly via a wired or wireless connection(s), and/or indirectly via the receiver 104/smart phone 108. In some example embodiments, server 120 may be implemented as a cloud-based server comprising at least one processor coupled to a network 160 such as the Internet, a cellular network, and/or the like.

Although FIG. 1 and some of the examples described herein describe the server 120 as a remote server processing heart rate data and/or other sensor data to determine MHR, other devices may process heart rate data and/or other sensor data to determine MHR as well. For example, the sensor 101, smart phone 108, and/or wrist-based device 104 (e.g., a smart watch) may include at least one processor and at least one memory including program code to process heart rate data and/or other sensor data in order to determine MHR as disclosed herein with respect to server 120.

Although FIG. 1 depicts a single sensor 101, there may be other sensors as well. For example, other sensors 104, 108, and/or the like may be used to gather audio from a subject, temperature data for the subject (or ambient temperature), and/or the like. These other sensors may be used to determine whether a subject is sleeping (which is when MHR is most likely to occur). Alternatively or additionally, a sensor, such as an accelerometer and/or the like, may be used to track a subject's movement. For example, if a subject is lying still for a period of time, then it is likely the subject is sleeping, and/or an audio sensor may detect snoring, which may be another indicator of a sleeping subject. Alternatively or additionally, a sensor, such as an accelerometer and/or the like, may detect that a subject is tossing or turning while sleeping. When this is the case, the server may flag data collected during this time as possibly noisy measurements (in which case the sensor may not use the heart rate measurements collected during the tossing and turning as likely unreliable data). Alternatively or additionally, a sleep sensor (which can be placed under a mattress for example) may be used as well to measure sound, ambient light, temperature, heart rate, breathing cycles, and/or the like. An example of such a sleep sensor is the Withings Aura Sleep Sensor, although other types of sensors may be used as well.

Although FIG. 1 depicts two receivers 104 and 108 (which may also serve as sensors), other quantities and/or types of receivers may be used as well. To illustrate, a first sensor may relay data to wrist-based receiver 104, while another sensor may couple to a smart phone 108. Alternatively or additionally, a tablet or computer may gather sensor measurements and upload data, via a wired or wireless connection to the server 120. Moreover, a sensor may upload data directly to the server 120. For example, a sensor 101 or an ECG sensor may upload its measurements for a given subject to server 120.

Even though MHR typically occurs while a subject is asleep, taking the minimum, measured heart rate while the subject is sleeping may not be suitable as that minimum measurement may not accurately reflect the subject's MHR. For example, a single measured heart rate corresponding to a minimum over a given sleep session may represent measurement noise or some other outlier measurement, rather than the subject's actual MHR. Moreover, during any given sleep session, a subject may not achieve a true MHR due to, for example, the subject being ill or other abnormal conditions or states associated with the subject or measurement conditions.

In some example embodiments, a processor, such as server 120, may, as noted, process heart rate data to determine whether a collected heart rate measurement is likely to represent a subject's MHR. As noted, although some of the examples refer to the server 120 collecting HR data and performing a determination of the MHR, other devices 101, 104, 108, and/or the like may, alone or in combination with server 120, may collect HR data and perform a determination of the MHR. For example, sensor 101 may measure heart rate, and include at least one processor and at least one memory to perform one or more aspects of processes 300-600 in order to determine a final MHR for a subject.

Figure 2A:
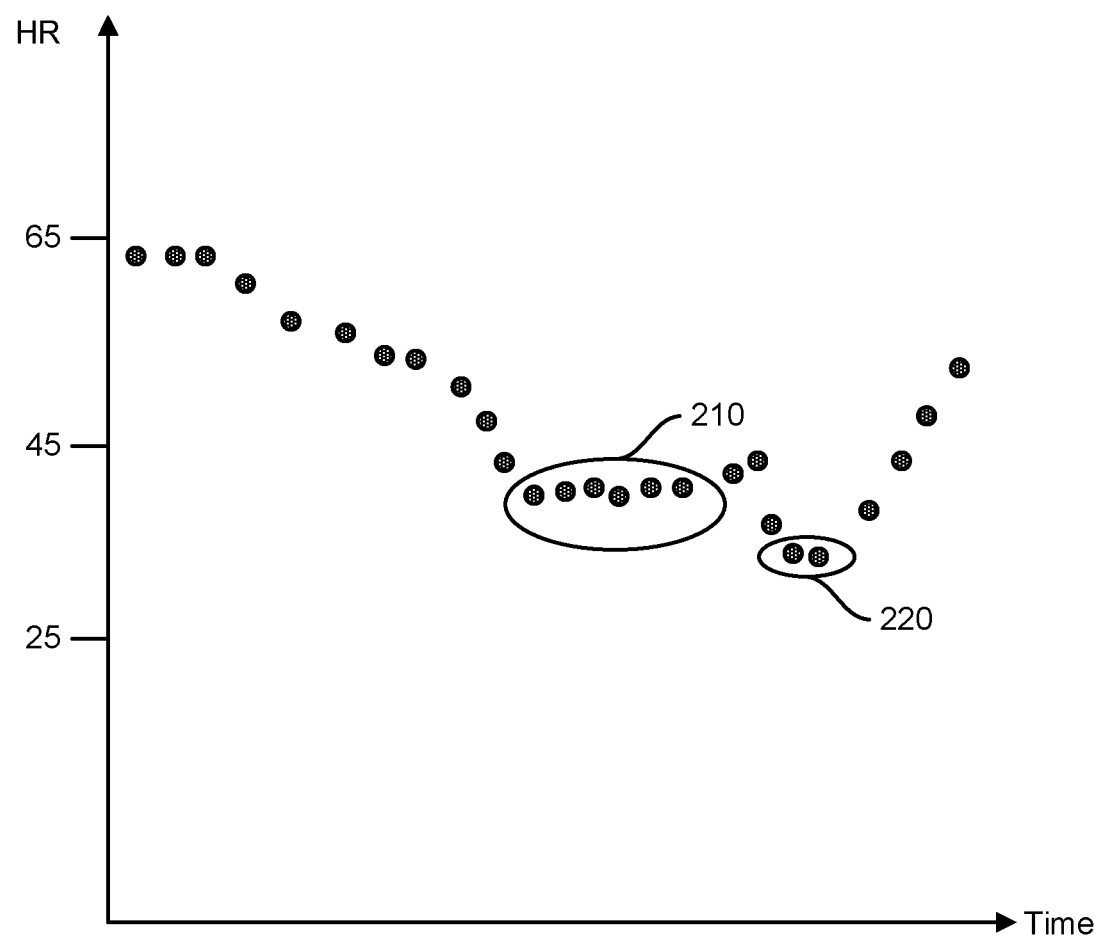
FIG. 2A depicts a plot of heart rate measured by a sensor over time, in accordance with some example embodiments.

In some example embodiments, heart rate data collected over a period of time may be processed by the server 120 using a predefined duration criteria of, for example, $T_d$ seconds. For example, if a subject's heart rate (HR) reaches a minima and represents a possible MHR value, a predetermined duration criteria of, for example, $T_d$ seconds may be applied to determine whether the possible MHR value is likely to accurately estimate the subject's MHR. FIG. 2A depicts a plot of heart rate measured by sensor 101 over time. While a subject is sleeping, the measured heart rate over time may vary from a low of 30 beats per second to 80 beats per second, as shown in FIG. 2A. However, the 30 beats per second may have occurred for a duration of less 5 seconds (see, e.g., FIG. 2A at 220), so in this example the 30 beats per second may not represent a likely MHR measurement as the 30 beats per second did not satisfy the predetermined duration criteria (which in this example is $T_d$ seconds equals 60 seconds). Supposing however that in the time series of HR data, there is a 120 second zone (or patch or interval) of HR data at 40 beats per second (see, e.g., FIG. 2A at 210). In this example, the 40 beats per second may be more likely to represents the subject's MHR as the 40 beats per second did satisfy the predetermined duration criteria of for example 10 seconds ($T_d$), although other criteria values may be used as well. In this way, the heart rate data may be processed in the time domain by at least applying a predetermined duration criteria ($T_d$) to the time series data representative of heart rate. As such, the predetermined duration criteria may provide time domain filtering of a data set of heart rate measurements for a given subject. This type of filtering may provide a more accurate indication of MHR, when compared to approaches that do not use such filtering.

Although the previous example provided example values for heart rates and MHR duration criteria ($T_d$), these values are merely examples as other values may be used as well. For example, MHR duration criteria ($T_d$) may vary between 5 seconds to 1 minute or more, although other durations may be used as well. In some example embodiments, the MHR duration criteria ($T_d$) may be selected based on certain factors, such as age of a subject, overall subject health, heart rate sensor being used, and/or other health or fitness related factors. In some example embodiments, the MHR duration criteria ($T_d$) may comprise a range, so that HR data values outside the range are filtered out. For example, given a MHR duration criteria ($T_d$) range of 5 seconds to 30 seconds, patches of HR data values outside the range that are less than 5 seconds may be filtered out, while patches of HR data values between 5 and 30 seconds may be further processed. Moreover, HR data in patches longer that 30 seconds may be filtered out as well.

Figure 2B:
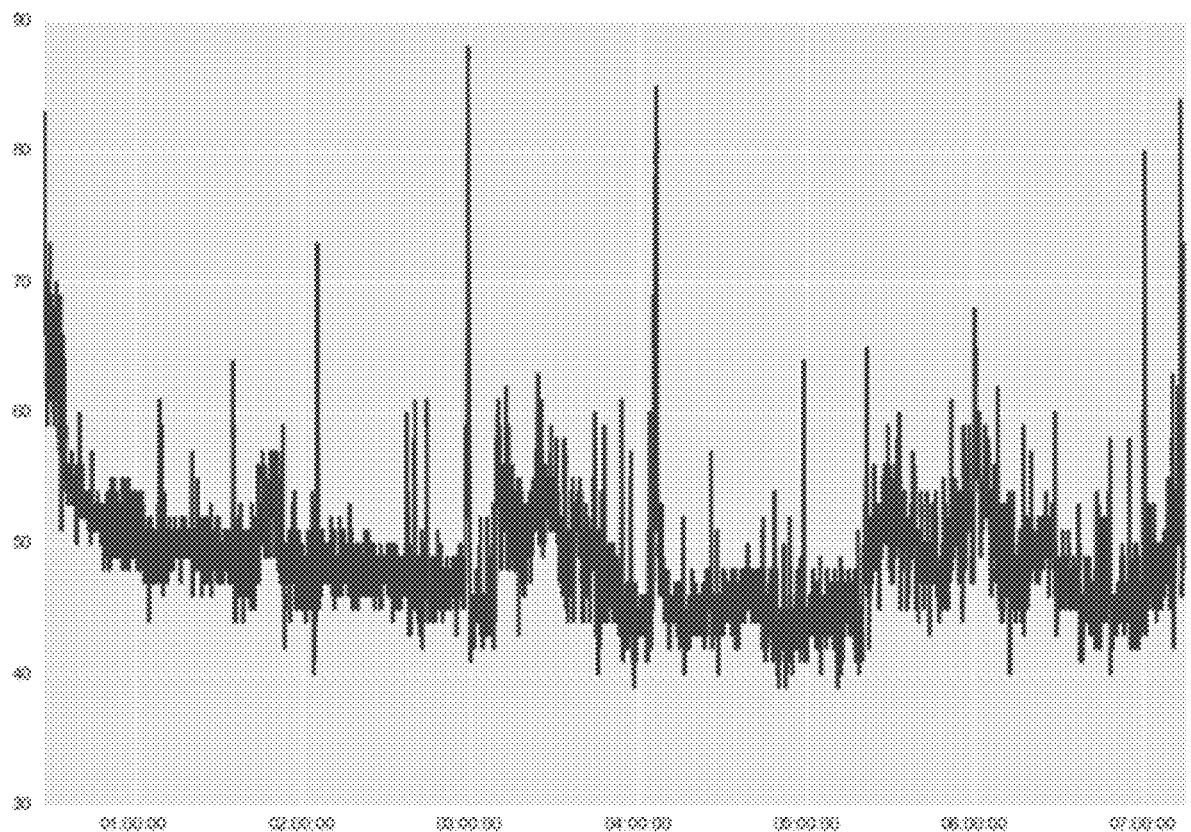
FIG. 2B depicts a plot of heart rate measured by sensor over time, in accordance with some example embodiments.
Figure 2C:
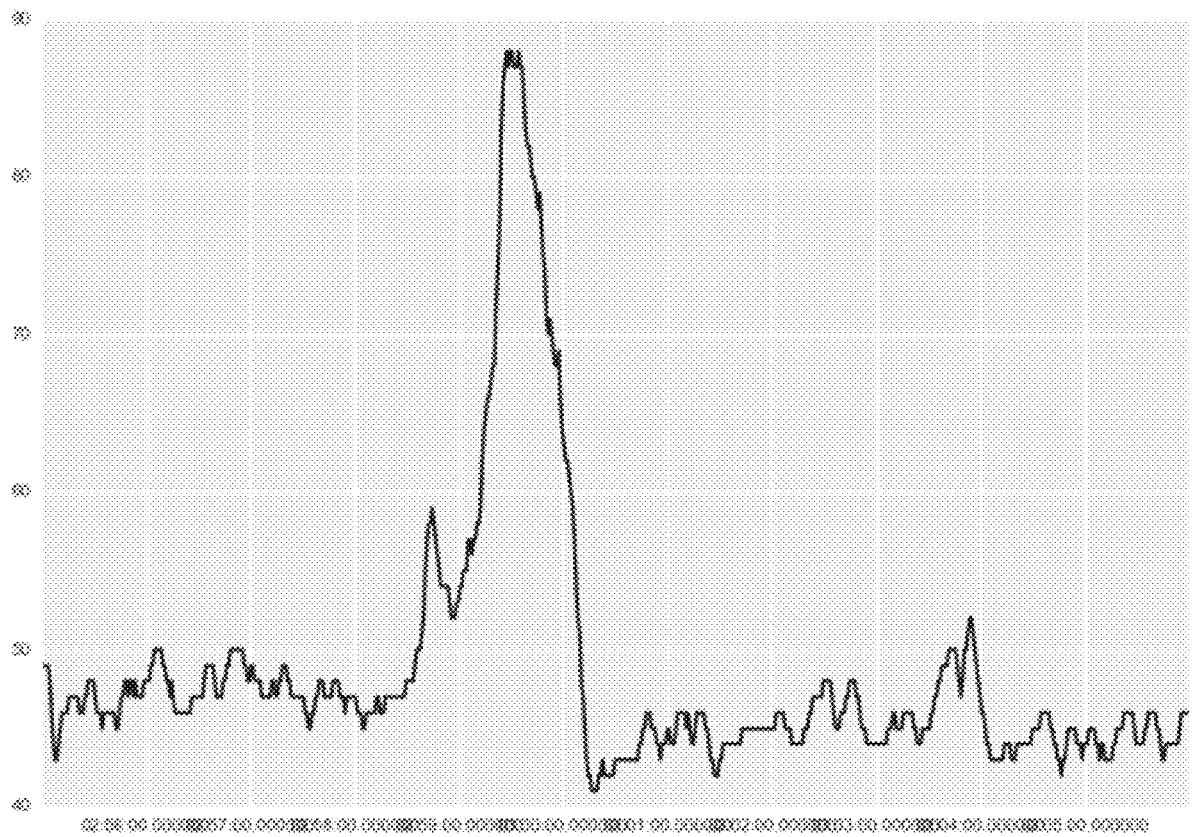
FIG. 2C depicts a zoomed in view of a portion of the plot of FIG. 2B, in accordance with some example embodiments.

FIG. 2B depicts another plot of heart rate measured by sensor 101 over time, while FIG. 2C depicts a zoomed in view of a portion of the plot of FIG. 2B. In both plots, the y-axis represents heart rate in beats per minute, while the x-axis represents time.

The value of the MHR's duration criteria ($T_d$) may be (1) predetermined, (2) specified based on experimental/clinical data, (3) derived from past heart rate or MHR measurements, and/or (4) established in other ways as well. To determine the MHR's duration criteria ($T_d$) dynamically, the bandwidth of the troughs (as shown for example in FIGS. 2B-C) of the HR time-series data may be determined. If x is a local minimum, then the value x plus a given value exists, wherein the delta may be a small positive number (e.g., 2 although other values may be used as well). The falling and rising slopes of the local time-series HR data values may be analyzed to determine the time difference between t2 and t1, where in t0 equals a time when the local minimum occurs, t1 equals the closest time before t0 when x plus the delta occurs, and t2 is the closest time after t0 when x plus delta occurs. By computing the bandwidth (t2−t1) in each local minimum (or trough), a statistical mode or median may be used to estimate $T_d$ dynamically. Alternatively or additionally, the MHR's duration criteria ($T_d$) may be pre-initialized to a given value. Over time the MHR's duration criteria ($T_d$) may be adjusted up (or down) based on the processing at 400. For example, the MHR's duration criteria ($T_d$) may be set to 60 seconds (although other values may be used as well), and, based on processing runs at 400, adjusted (within limits such as a minimum allowable the MHR's duration criteria ($T_d$) and/or a maximum the MHR's duration criteria ($T_d$)).

In some example embodiments, a process may collect HR measurements from one or more sensors 101, 104, 108, and/or the like over a time and then use the HR measurements to determine (e.g., estimate, calculate, derive, and/or the like) the MHR of the subject. Furthermore, the determined MHR may be used to further determine other health and/or fitness parameters for the subject.

Referring again to FIG. 1, system 100 may collect HR data measured by sensor 101, for example. The collected HR data may be stored at server 120. The database 135 may store, for a given subject, heart rate data as well as other data for the subject. To illustrate further, each subject may be assigned a user identifier (ID). Heart rate data for a given session may be received at server 120 and stored at database 135 for the given subject under the subject's user ID. Moreover, other sensor data including sleep state related information (e.g., data indicative of whether the subject is awake or asleep), subject profile information (e.g., age, weight, body fat percentage, blood pressure, and/or the like) may also be stored under the user's ID.

In some example embodiments, the database 135 may store HR data and/or other data based on session, such as whether the data is associated with a sleep session or an awake session. For example, a session ID (or other type of indicator) may be assigned to each session, so that the HR data and other data collected for that session can be processed together as a session. Moreover, the server 120 may determine, from the HR data and/or other data stored at database 135, a MHR, and the MHR may also be mapped to the user ID. When this is the case, a query to server 120 indicating a user ID and/or time period may be responded to with a MHR value and/or other MHR derived health and/or fitness parameters for the subject corresponding to the user ID. Although the database 135 is shown in server 120, the database may be implemented in other locations and/or may be distributed among devices as well.

To illustrate further, data collected from a subject including HR data, sleep state data, and/or other data collected regarding the subject may be processed by server 120 to determine a MHR for the subject. In some example embodiments, the server 120 may provide a service, such as a cloud-based service, to collect and/or determine MHR and/or other parameters for one or more subjects, although the server 120 (and corresponding persistence such as database 135) may be implemented in other devices as well including a user equipment, such as a smartphone, tablet, and/or the like including devices 101-104, for example.

The server 120 may receive a query requesting a MHR for a subject having a certain user ID. The query may also indicate a time frame over which the MHR should be provided. Based on this query, the server 120 may fetch relevant session datasets from the database 135, and perform a MHR determination using the fetched datasets. The server 120 may also fetch, based on the subject's ID, additional user profile parameters, such as age, weight, and/or the like. The server 120 may respond to the query with a MHR (also referred to herein as the "final" MHR) for the subject identified by the subject's ID. The response may also include other health and fitness related parameters determined from the MHR.

Figure 3:
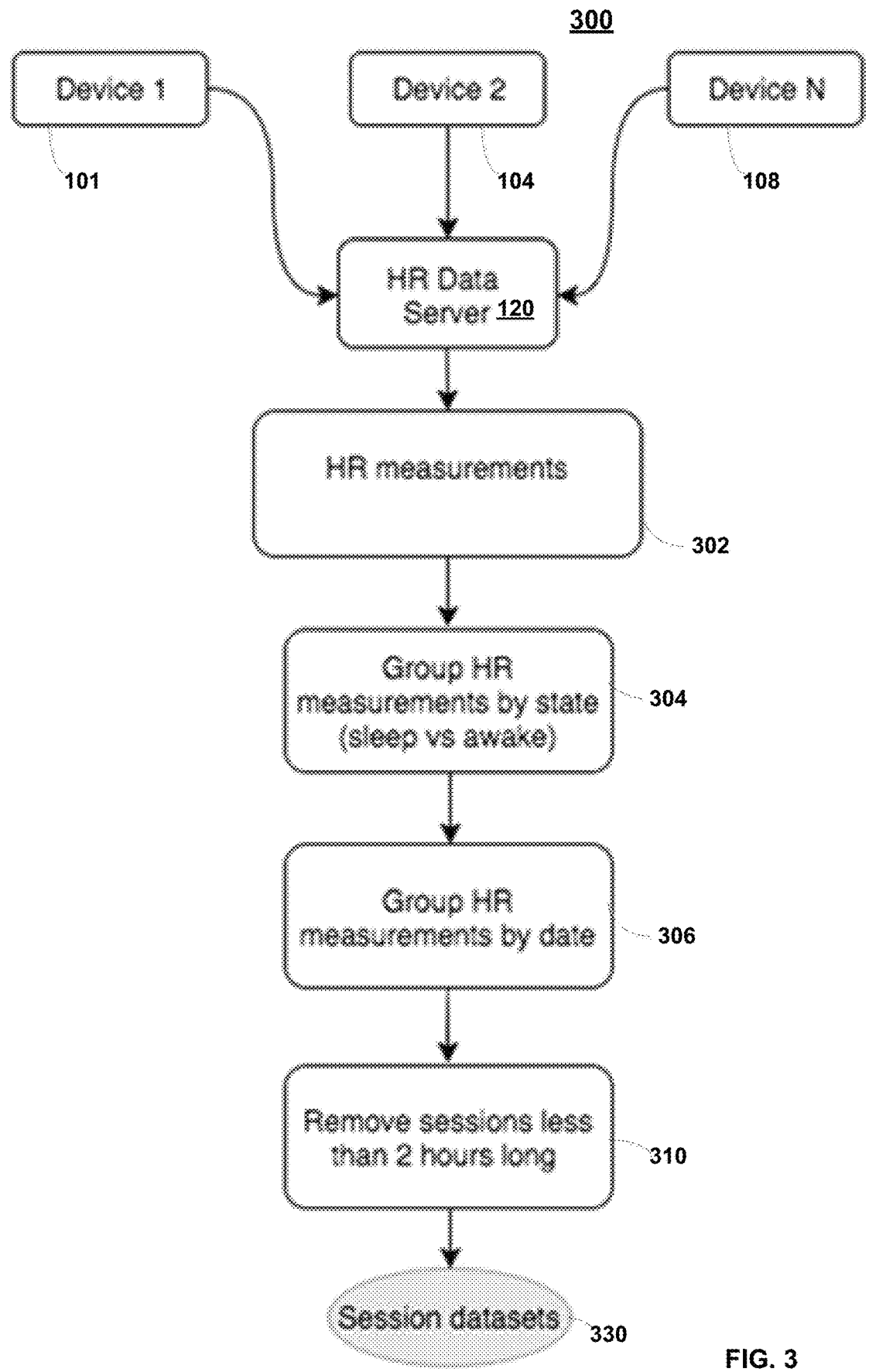
FIG. 3 depicts an example of a process for pre-processing data into session data sets, in accordance with some example embodiments.

FIG. 3 depicts an example of a process 300 for pre-processing data (e.g., HR data as well as other data) into session data sets, in accordance with some example embodiments.

At 302, the server 120 may receive data, in accordance with some example embodiments. The data may include HR data obtained from a sensor, such as sensor 101, for example. The data may also include other data obtained from other sensors, such as sensors 104, 108, and/or other devices/sensors. For example, the other data may include data indicative of the subject's sleep state as well as other types of sensor data. Moreover, data collected from a subject may be stored so that it has indication of when the data was collected or measured. For example, HR data measurements may each have a time stamp indicating when the measurement data was collected or measured by sensor 101. Likewise, other data, such as data indicative of the subject's sleep state (e.g., whether the subject is awake or asleep), may also include a time stamp indicating when the measurement data was collected. In some example embodiments, the server 120 may store the received data for each subject based on a user ID, so that processing can be performed for a given subject associated with the user ID.

At 302, the server 120 may process the received data according to session start and/or end times, in accordance with some example embodiments. For example, server 120 may combine received HR and other data for a given subject and group the data based on sessions, so that data corresponding to the same session is grouped together (although the server may also just flag or indicate which session data belongs to). At this point, data for each session is grouped together either by a sort or by an indicator.

At 304, the server 120 may indicate or determine whether data is associated with a sleep session of the subject or an awake state of the subject, in accordance with some example embodiments. As noted above, sensor data may indicate whether the subject was sleeping (e.g., supine, snoring, time of day, the heart rate measurements themselves, etc.). This data can be used to indicate whether a session is a sleep session or an awake session. Moreover, an indicator, such as a session ID, flag, and/or the like, may be generated to identify whether a session is a sleep session or an awake session. Moreover, a session ID may be generated to identify a session. In this way, data for each session can be identified and grouped for further processing.

The server 120 may, at 306, group, sort, or flag sessions by date, in accordance with some example embodiments. For example, the data sets associated with sleep session may be sorted or grouped by date.

At 310, the server 120 may then mark or delete any sessions, such as sleep session that are shorter than a predefined session time, such as 2 hours (although other time durations may be used as well). In some example embodiments, a minimum sleep session duration may be configured. For example, the minimum sleep session duration may be set at 2 hours as that is a time during which a subject is more likely to achieve deep sleep and thus likely to attain an MHR state. In this way, sessions that are too short to allow the subject to reach a state where MHR can be obtained are marked or filtered out to avoid further processing.

At 330, the data sets at 330 may thus represent received HR and other data that have been processed to data sets associated with sleep states or awake states. Alternatively or additionally, the data sets may be processed to ensure each session is longer than a predetermined session time. Alternatively or additionally, the data sets may be grouped or sorted by date and/or time. These data sets 330 may then be further processed at FIGS. 4-6 to determine a MHR, in accordance with some example embodiments.

Figure 4:
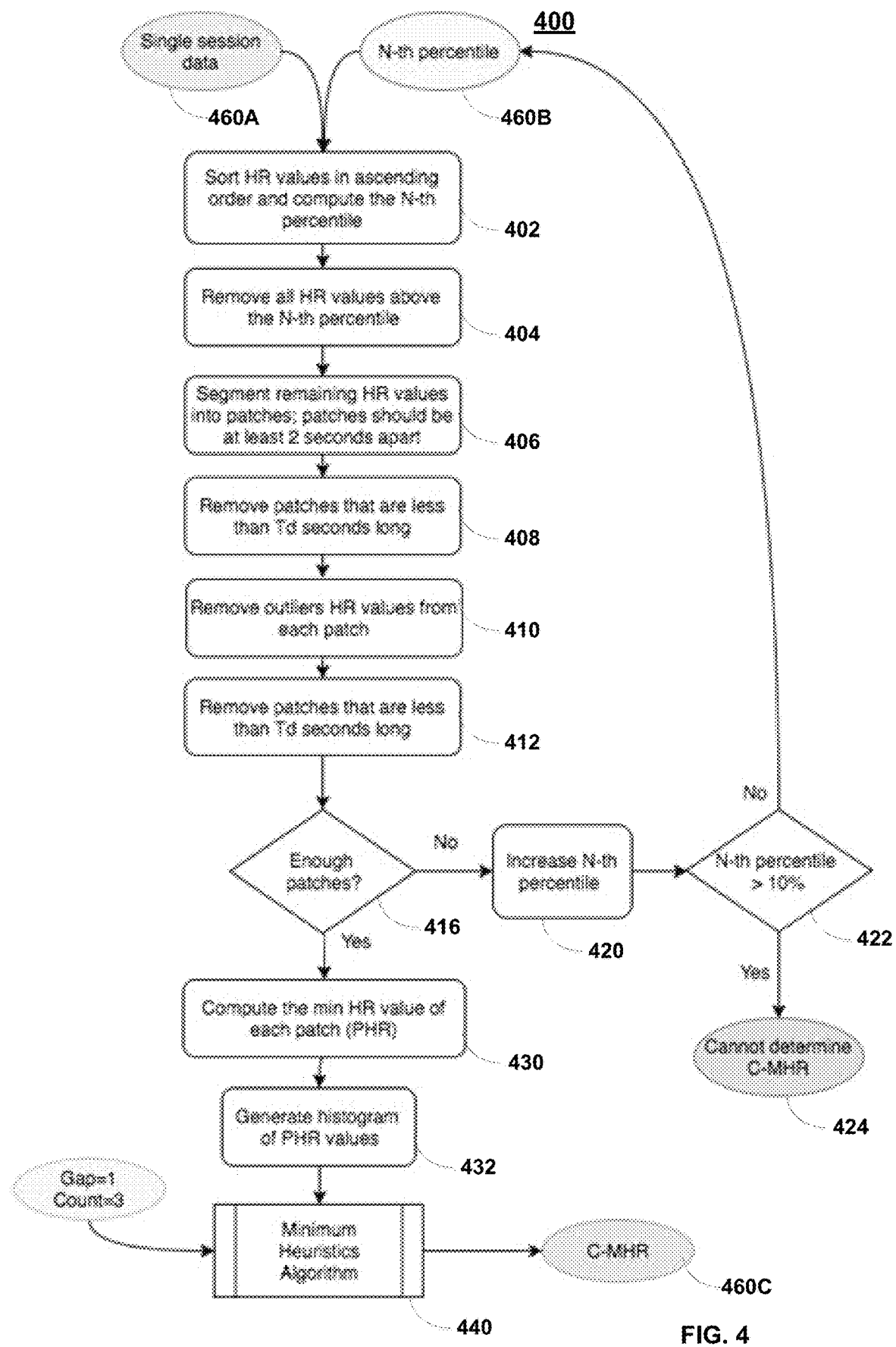
FIG. 4 depicts an example of a process for determining a candidate minimum hear rate (MHR), in accordance with some example embodiments.

FIG. 4 depicts an example of a process 400 for determining a candidate MHR, in accordance with some example embodiments.

The server 120 may also determine, for each session dataset generated using process 300, a single, local estimate of MHR, which is referred to herein as a candidate MHR. The candidate MHR may be characterized as a minimum heart rate that was determined from a zone or a time interval (also referred to herein as a patch) satisfying the predetermined duration criteria ($T_d$). Alternatively or additionally, the candidate MHR may be characterized as a repeatable measurement. For example, the candidate MHR may need to occur a plurality of times in the session data set. To illustrate further, for a minimum HR value to be classified as a candidate MHR value, the HR value may need to occur at least 3 times for example in the session dataset.

Given a session data set 460A, the process 400 may determine a candidate MHR 460C for the given session. For example, a session may represent a sleep session or an awake session during which HR data is collected and grouped into a session.

Figure 2D:
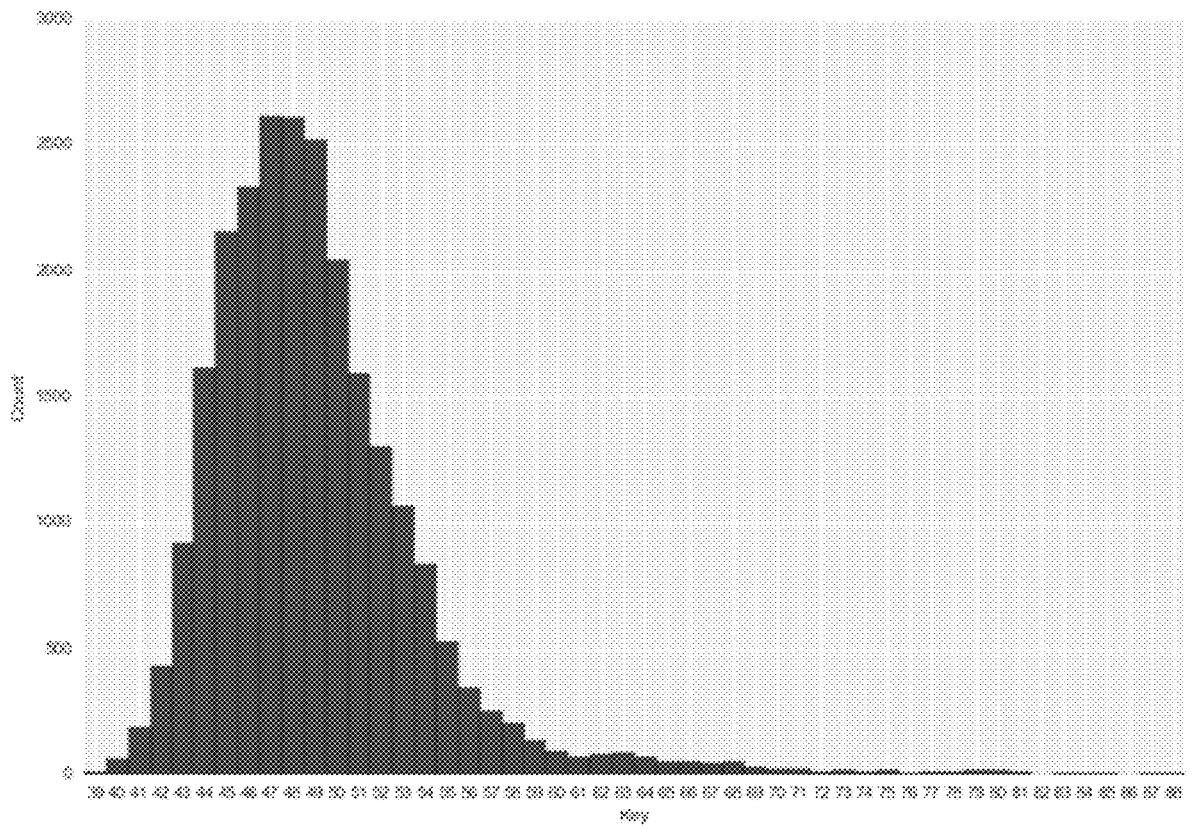
FIG. 2D depicts an example of a histogram of heart rate values for an entire sleep session sorted in ascending order, in accordance with some example embodiments.
Figure 2E:
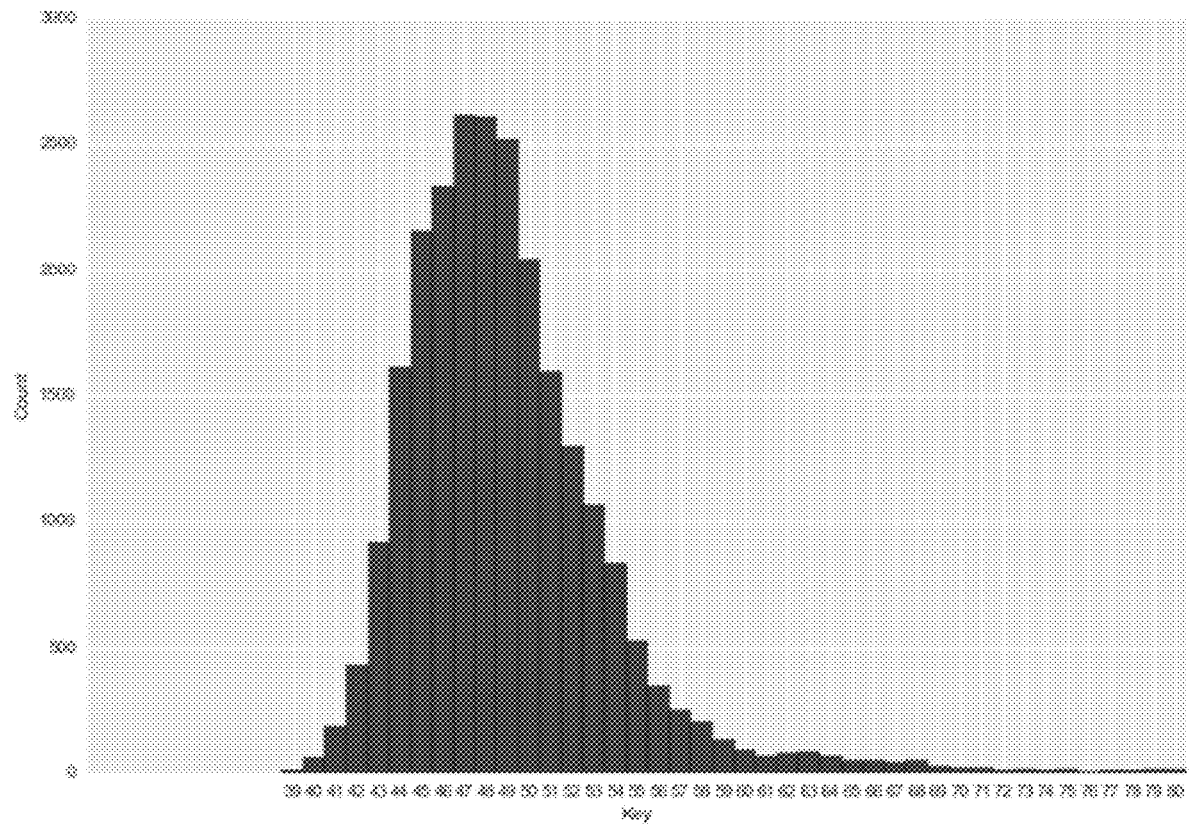
FIG. 2E depicts the histogram of FIG. 2D but thresholded to a range of 30 to 80 beats per minute (bpm), in accordance with some example embodiments.

At 402, the server 120 may receive a HR data set 460A for a single session and sort the received HR values in for example ascending order, in accordance with some example embodiments. FIG. 2D depicts an example of a histogram of HR values for an entire sleep session, which has been sorted in ascending order. At FIG. 2D, the minimum recorded HR is 36 while the maximum recorded heart rate is 88. FIG. 2E depicts the histogram of FIG. 2D but thresholded to a range of 30 to 80 bpm. Referring again to FIG. 4, the server 402 may then determine, or be provided with, an $N^{th}$ percentile 460B. For example, the $N^{th}$ percentile can be initialized at a given value, such as 0.01%, and then used to obtain a threshold HR value from the histogram of raw HR values. The initial $N^{th}$ percentile may be adjusted dynamically over time as process 400 is performed (which may include threshold limits to the value of the $N^{th}$ percentile as depicted at FIG. 4 at 422).

At 404, the server 120 may remove any HR values above the $N^{th}$ percentile, in accordance with some example embodiments. As such, only those HR measurements in the session time-series data that are at or below the $N^{th}$ threshold are kept, and the HR measurements above the threshold are removed from the data set. Referring to FIG. 2D again, applying the $N^{th}$ threshold percentile of 0.01% gives a HR threshold of 39, which when applied on the HR data results in no patch satisfying the $T_d$ condition at 416 (as described below), so the $N^{th}$ threshold percentile may be incremented to for example 1.51% for a second pass. In this case, the revised $N^{th}$ threshold percentile yields an HR threshold of 42, and 45 patches for example.

At 406, the server 120 may group the remaining HR values into clusters, or patches of HR measurements, in accordance with some example embodiments. Table 1 depicts patches 0-2. The server 120 can proceed through all of the remaining HR values and associate them with a cluster or patch.

TABLE 1

| datetime | hr | in_sleep |
|---|---|---|
| Patch 0 duration: 8 secs (only first 5 secs shown) | | |
| 2016 Apr. 27 02:04:09.842 | 42 | True |
| 2016 Apr. 27 02:04:10.833 | 42 | True |
| 2016 Apr. 27 02:04:11.825 | 41 | True |
| 2016 Apr. 27 02:04:12.815 | 41 | True |
| 2016 Apr. 27 02:04:13.832 | 40 | True |
| Patch 1 duration: 6 secs (only first 5 secs shown) | | |
| 2016 Apr. 27 02:04:20.825 | 42 | True |
| 2016 Apr. 27 02:04:21.815 | 42 | True |
| 2016 Apr. 27 02:04:22.833 | 41 | True |
| 2016 Apr. 27 02:04:23.825 | 41 | True |
| 2016 Apr. 27 02:04:24.815 | 41 | True |
| Patch 2 duration: 6 secs (only first 5 secs shown) | | |
| 2016 Apr. 27 02:42:56.708 | 42 | True |
| 2016 Apr. 27 02:42:57.698 | 42 | True |
| 2016 Apr. 27 02:42:58.718 | 42 | True |
| 2016 Apr. 27 02:42:59.708 | 42 | True |
| 2016 Apr. 27 02:43:00.698 | 42 | True |

At 408, any patches less than the predetermined duration criteria ($T_d$) may also be removed from the data set, in accordance with some example embodiments. Given a predetermined duration criteria of 2 seconds ($T_d$ equals 2 second), any patch of HR data that has a duration of less than 2 seconds may be removed or filtered out of the data set.

At 410, outlier analysis may be performed, in accordance with some example embodiments. For example, an outlier analysis may be applied to each of the patches or groups of HR data to determine whether in a given group/patch, any of the HR values are an outlier. The outlier may remove from any given patch/cluster HR values that are spuriously high and low. To determine an outlier, statistical techniques can be applied. For example, if any given HR value in a patch exceeds a median or an average HR for the patch, the HR value may be removed from the patch. Moreover, the HR value that exceeds a threshold value, such as a fixed value or a standard deviation from the average/mean/median, may be removed. Although the previous example describes the use of standard deviation to identify an outlier in a patch, other outlier techniques may be used as well.

After the outliers are removed, the server 120 may, at 412, perform another check of the remaining patches to determine if the remaining patches still satisfy the predetermined duration criteria ($T_d$), in accordance with some example embodiments. If not, the patch may be removed. For example, if the removal at 410 of an HR value makes a patch less than the predetermined duration criteria ($T_d$), that patch may be filtered out of the session data set.

In some example embodiments, the server may check, at 416, to see if there is a sufficient quantity of patches to continue processing, in accordance with some example embodiments. For example, if there are not a sufficient quantity of patches having HR data (e.g., the quantity of patches is less than a threshold quantity), the server 120 may increase, at 420, the $N^{th}$ percentile to allow more HR values to be processed at 402-412. In the example of FIG. 4, the $N^{th}$ percentile may not be increased over a maximum $N^{th}$ percentile, which in this example is 10%, as shown at 422 and 424 (although values other than 10% may be used as well).

At 430, the minimum heart rate of each patch (referred to herein as a patch HR) may be determined, in accordance with some example embodiments. At 432, a histogram of the patch HRs may be generated. The histogram 432 of patch HRs may be further processed, at 440, to determine a minimum for the session, in accordance with some example embodiments. In some example embodiments, the server 120 may process the histogram of patch HRs using a minimum heuristics algorithm (MHA) to estimate a candidate MHR at 406C for the session data set input at 460A. The minimum heuristics algorithm is described further with respect to FIG. 6.

Figure 5:
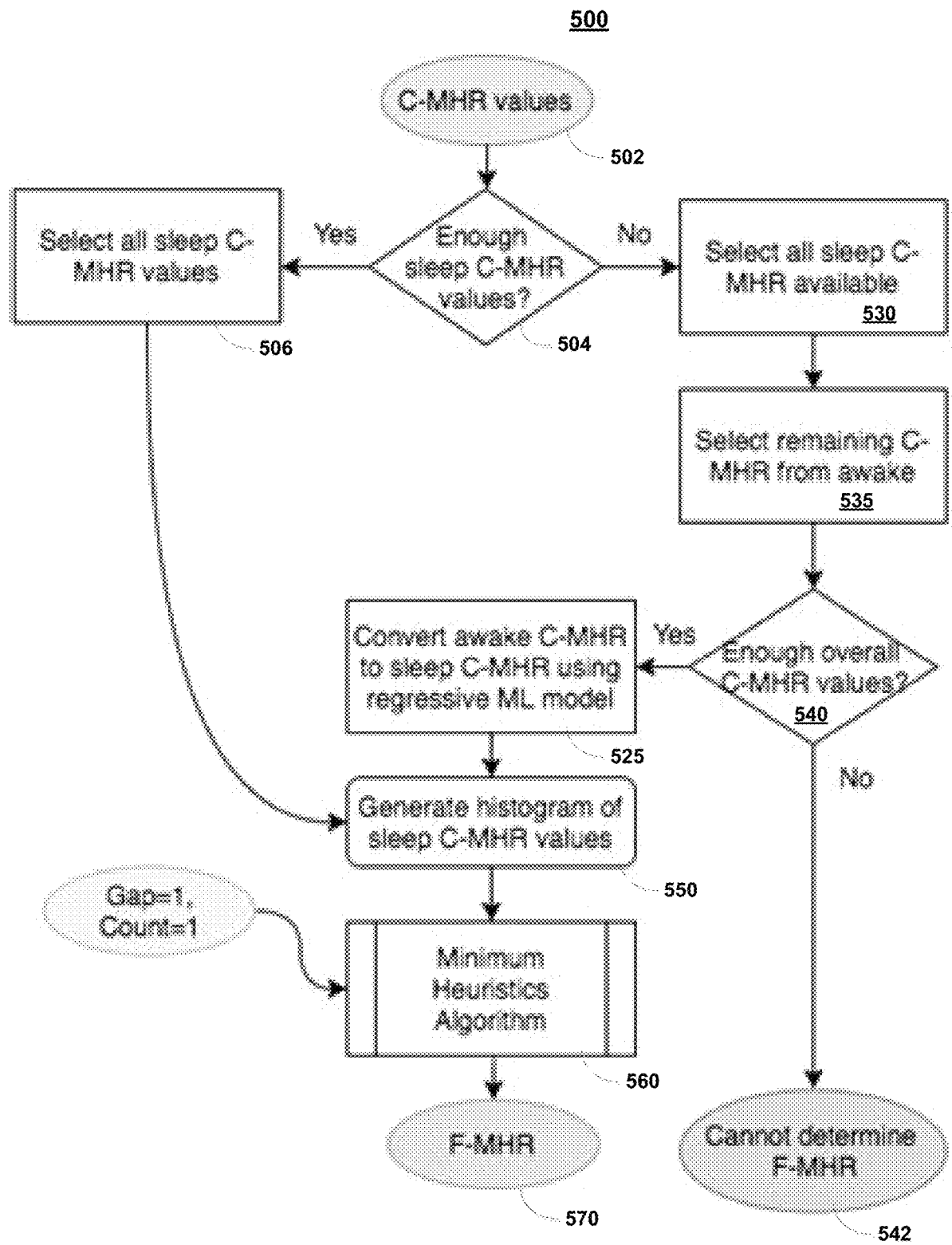
FIG. 5 depicts an example of a process for determining a final MHR, in accordance with some example embodiments.

FIG. 5 depicts an example of a process 500 for determining the final MHR that can be provided in response to the query for a subject's MHR, in accordance with some example embodiments.

For a given subject, the server 120 may have a plurality of HR data sets, each of which may correspond to a different session. The server 120 may process each of these HR data sets using process 300 to determine a candidate MHR for each session. Process 500 may process the candidate HR values from the different sessions, and attempt to determine a so-called "final" MHR value.

At 502, the server 120 may receive the candidate MHR values for a plurality of sessions. For example, the server may receive a plurality of candidate MHR for sessions occurring over a week, month, or other time frame. The candidate MHR may correspond to sleep and/or awake sessions.

Figure 2F:
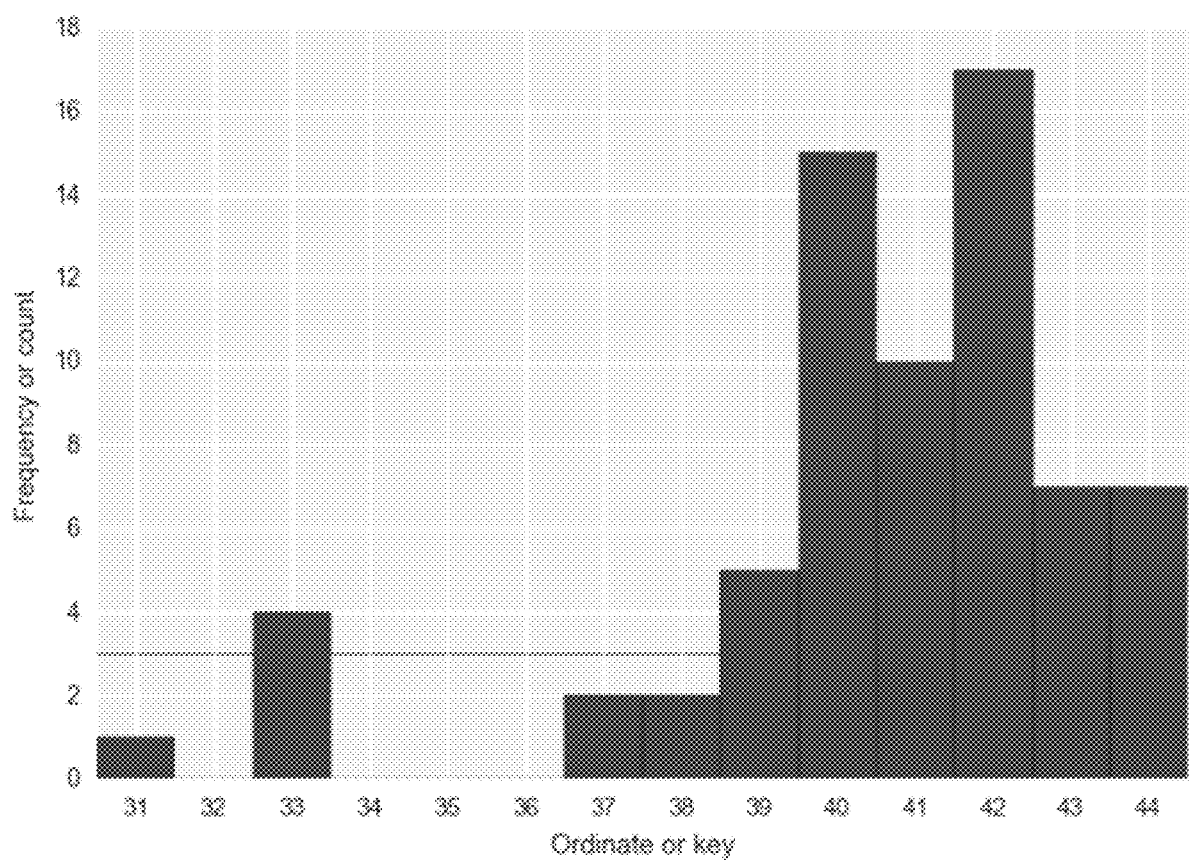
FIG. 2F depicts an example histogram of candidate HR values, in accordance with some example embodiments.

If the quantity of candidate MHR values from sleep sessions is sufficient (e.g., exceeds a predetermined quantity), the server 120 may generate a histogram of the candidate HRs (yes at 504, 506, and 550). FIG. 2F depicts an example histogram of candidate HR values. In the example of FIG. 2F, the candidate HR values are plotted on the x-axis and the corresponding frequency of occurrence is on the y-axis. The histogram may be further processed, at 560, to determine a suitable minimum from among candidate MHRs. In some example embodiments, the server 120 may determine a suitable minimum from among candidate MHRs using a minimum heuristics algorithm to estimate a final MHR at 570 for the sleep session data set being processed.

If the quantity of candidate MHR values from sleep sessions is insufficient (e.g., is less than a predetermined quantity), the server 120 may use the candidate MHR values from awake sessions to determine sleep session candidate MHR values. Specifically, the server 120 may estimate candidate MHR values based on candidate MHR values obtained from awake sessions. In some example embodiments, the server 120 may estimate, from an awake session data set, a sleep state candidate MHR value using machine learning, such as a regression machine learning model. When this is the case, each awake state candidate MHR value can be converted, using the model, to a sleep candidate MHR value. This model may be pre-trained based on known awake candidate MHR and sleep candidate MHR pairs across a training set of individuals or it could be customized for each individual as well. After the conversions are complete, a single set of sleep candidate MHR values (composed of actual candidate MHR values and candidate MHR values derived from awake state data) may be process at 560 to determine the final MHR value 570.

Referring to 530, the server 120 may fetch the sleep state candidate MHR values available for a given subject, and fetch at 535 one or more awake state candidate MHR values for the given subject. If there are a sufficient quantity of candidate MHR values (e.g., exceeding a threshold quantity), the server may, at 540, convert one or more awake state candidate MHR values into sleep state candidate MHR values, as noted above. At this point, the process may continue to determine a final MHR using the actual sleep state candidate MHR values and the "converted" awake state candidate MHR values.

If there are an insufficient quantity of candidate MHR values (no at 540), the server may, at 542, choose not to calculate a final MHR value.

Figure 6:
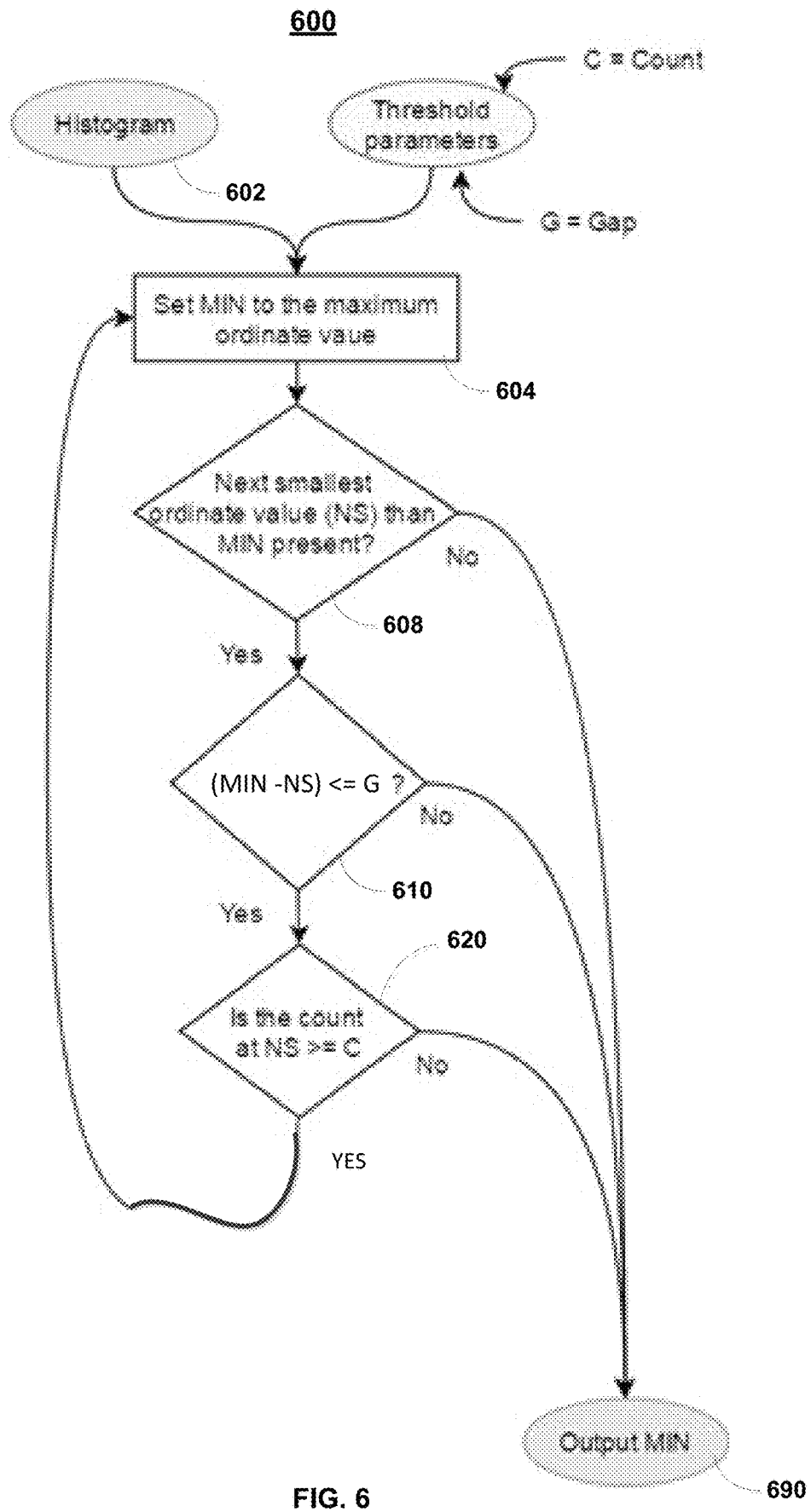
FIG. 6 depicts a process for determining a minimum heart rate from a plurality of candidate minimum heart rates, in accordance with some example embodiments.

In some of the example embodiments, the final MHR value is determined using a minimum heuristics algorithm. FIG. 6 depicts a process 600 for an example implementation of a minimum heuristics algorithm, in accordance with some example embodiments. However, the final MHR value may be determined from a plurality of candidate MHR values in other ways. For example, a minimum from among a plurality of candidate MHR values may be selected as a final MHR. In some example embodiments, a minimum candidate MHR value that is found repeatedly (e.g., exceeding a threshold value of counts) in the candidate MHR data may be used as the final MHR value for the subject. Alternatively or additionally, the $N^{th}$ percentile (e.g., $10^{th}$) of the candidate MHR values after they are sorted low to high may be used as the final MHR.

Although the minimum from among a plurality of candidate MHR values may be selected as a final MHR minimum value, this approach can under estimate the true minimum heart rate of a subject. Accordingly, process 600 may be used to determine a final MHR.

The server 120 may receive, at 602, a histogram including frequency counts (y-axis) plotted against ordinate values (x-axis). The server may also receive, at 604, threshold parameters, such as a count (C) and a gap (G). The server 120 may seek to pick an ordinate value that best satisfies the conditions for the minimum. To that end, process 600 may use two threshold parameters to enforce these conditions, namely (1) count, and (2) gap. The count threshold (C) may specify the minimum frequency of occurrence of the minimum value, which in a sense provides an indication of a repeat minimum measurement. This may eliminate candidate minimum values, which occur only once or fewer times than the count threshold. The gap threshold (G) may specify the minimum continuity between candidate values for passing on the title of the current minimum. In most situations, a gap of 1 may be suitable, but this may be increased based on the application at hand.

Referring to FIGS. 2F and 6, a maximum ordinate value may be selected, at 604. For example, the value 44 may be selected from the histogram of FIG. 2F and set as a minimum (MIN). At 608, if the next smallest (NS) is present in the histogram, then the next smallest value may be selected, which in this example is 43. At 610, if the difference between the set minimum (44) and the next smallest (43) is less than or equal to the gap which in this example is 1, then a count threshold is performed at 620. At 620, if the next smallest is greater than or equal to the count, which is 3 in this example, then the next smallest is set as the minimum at 604 and the process repeats (yes at 620 and 604). If the next smallest value in the histogram is not greater than or equal to the count, the current smallest value is declared as the final MHR.

The following provides additional example of other health and fitness parameters that can be determined from the final MHR determined in accordance with some example embodiments.

In some example embodiments, target heart rates for different training zones may be determined based on the final MHR. When that is the case, the objective is to determine, from the final MHR, the range of heart rates a person should maintain when exercising in training zones. For example, the following can be treated as training zones: (1) recovery zone (60-70% of THR), (2) aerobic zone (70-80% of THR), and (3) anaerobic zone (80-90% of THR). Target Heart Rate (THR) is calculated the Karnoven formula as follows:

THR=(maxHR−MHR)×training %+MHR, wherein MaxHR refers to maximum heart rate, which can be computed as follows: maxHR=207−0.7*Age of the Subject.

In some example embodiments, VO2 max and calories burned may be determined (e.g., for a given exercise) based on the final MHR. For example, the VO2 max may be the maximum amount of oxygen (in milliliters (mL)) consumed per unit mass of a person's body mass while exercising in one minute. The $U^{th}$-Sorensen-Overgaard-Pedersen formula estimates VO2 max using:

$$VO2\ max = 15.3 \times \frac{maxHR}{MHR}.$$

The HR of a subject can drop during sleep and can be near the minimum heart rate during deep sleep. If the MHR is known, then it could be used to classify deep and light sleep regions based on the HR time-series. For example, deep sleep may be classified as follows: MHR≤HR≤1.15×MHR, while light sleep may be classified as follows: 1.15×MHR<HR≤1.30×MHR.

In some example embodiments, the server 120 may estimate, based on the final MHR, stressful periods. For example, during a stressful period, the HR of a subject can elevate, followed by other changes (such as breathing rate increases, sweating, etc.). The MHR may be used to identify potentially stressful periods based on the HR time-series data. Furthermore, if the breathing rate or other information has also been determined in other ways, the server may classify a time period as potentially stressful based on the following: 1.80×MHR≤HR.

Referring again to FIG. 1, the processing of the HR data as described herein may be performed in a distributed manner, in accordance with some example embodiments. For example, one or more portions of process 300, 400, 500, and/or 600 may be distributed among one or more devices, such as sensors 101-108, server 120, and/or other processor and memory based devices. For example, the server 120 may provide configuration information to one or more sensors, such as sensor 104, 101, and/or the like. This configuration information may include the threshold parameter for the $N^{th}$ percentile, $T_d$ duration, and/or the like. In this example, the sensors, such as sensor 104 and sensor 101, may use the configuration information and any stored HR data to determine a candidate MHR value for one or more sessions stored at the sensor. The sensors 101/104 may then report their corresponding candidate MHR values for a subject to a processor (e.g., server 120 or another device, such as smart phone 108, one or more of sensors 101/104 capable of performing the final MHR determination using for example, process 500).

Figure 7:
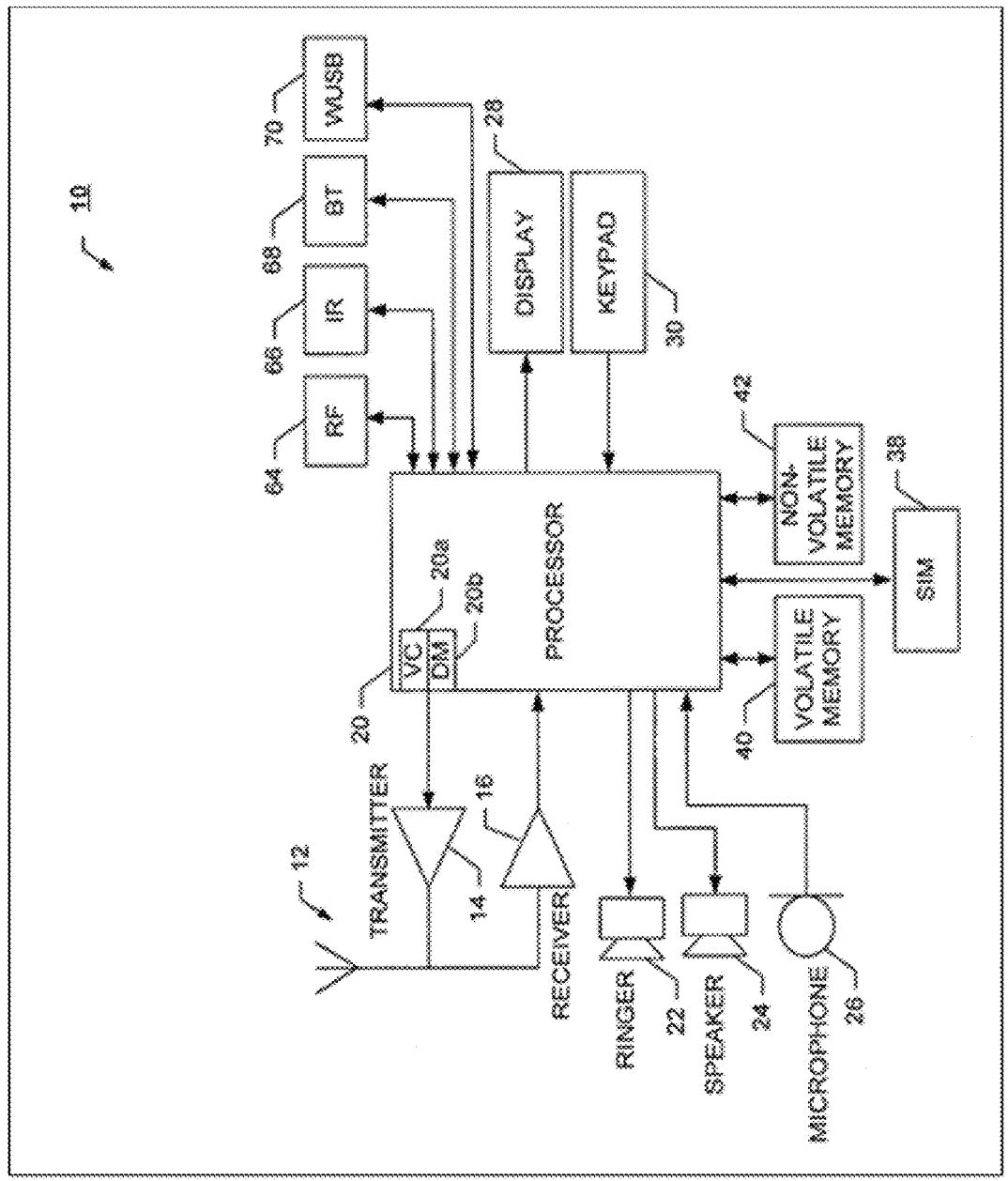
FIG. 7 depicts an example of an apparatus, in accordance with some example embodiments.

FIG. 7 illustrates a block diagram of an apparatus 10, in accordance with some example embodiments. The apparatus may be implemented as any type of device including a server, a computer, a wireless device, a smart phone, a cell phone, a machine type communication device, a wireless sensor, an Internet of things (IoT) device, and/or any other processor and memory based device. The apparatus 10 (or portions thereof) may be configured to provide receivers 104, 108, server 120, and/or sensor 101.

For example, apparatus 10 may be implemented as a user equipment such as a sensor 101 to measure over time heart rate, store the heart rate in a persistent store, such as a database, and then process the collected data into session data (as described with respect to process 300), determine candidate MHR values (as described with respect to process 400), and determine a final MHR values (as described with respect to process 500). Alternatively or additionally, one or more aspects of processes 300-600 may be performed by apparatus 10/sensor 101 or a remote server 120 as well. Alternatively or additionally, apparatus 10/sensor 101 may collect sensor data such as heart rate and forward, as noted, the collected data to the remote server 120 either directly or via another device, such as smart phone 108. Sensor 101 may include receiver circuitry configured to measure the electrical activity associated with a user's heart beats and/or a transmitter to transmit the measurements (in either raw form or processed into heart rate data and time stamps) to another device.

To illustrate further, apparatus 10 may be implemented as a user equipment such as a smart watch 104 which can perform a variety of measurements including heart rate, audio measurements, motion detection, and/or the like. When this is the case, smart watch 104 may store the heart rate in a persistent store, such as a database, and then process the collected data into session data (as described with respect to process 300), determine candidate MHR values (as described with respect to process 400), and determine a final MHR values (as described with respect to process 500). Alternatively or additionally, one or more aspects of processes 300-600 may be performed by smart watch 104 and/or a remote server 120 as well. Alternatively or additionally, smart watch 104 may collect sensor data and forward, as noted, the collected data to the remote server 120 either directly or via another device, such as smart phone 108.

Apparatus 10 may be implemented as a user equipment such as a smart phone 108 which can perform a variety of measurements including heart rate, audio measurements, motion detection, and/or the like. When this is the case, smart phone 108 may store the heart rate in a persistent store, such as a database, and then process the collected data into session data (as described with respect to process 300), determine candidate MHR values (as described with respect to process 400), and determine a final MHR values (as described with respect to process 500). Alternatively or additionally, one or more aspects of processes 300-600 may be performed by smart phone 108 and/or a remote server 120 as well. Alternatively or additionally, smart phone 108 may collect sensor data and forward, as noted, the collected data to the remote server 120 either directly or via another device.

In some example embodiments, apparatus 10 may receive a heart rate data set collected from a subject. The heart rate data may be provided from a sensor such as sensor 101, 104, and/or the like. Moreover, the heart rate data set may be collected by the sensor(s) over one or more sessions, which may include awake state sessions and/or sleep state sessions. The apparatus may, in some example embodiments, filter the heart rate data set to remove heart rate values failing to satisfy a predetermined duration threshold. In this way, heart rate values not likely to be an accurate representation of the subject minimum heart rate are removed from consideration. The apparatus may determine a minimum heart rate value from the filtered heart rate data and then provide the determined minimum heart rate (which may be in response to a query for the subject's minimum heart rate). The apparatus may filter the heart rate data set by at least applying an adaptive threshold to filter a histogram of the heart rate data set, so that heart rate data values above the adaptive threshold are removed.

In some example embodiments, the apparatus 10 may include at least one antenna 12 in communication with a transmitter 14 and a receiver 16. Alternatively transmit and receive antennas may be separate. The apparatus 10 may also include a processor 20 configured to provide signals to and receive signals from the transmitter and receiver, respectively, and to control the functioning of the apparatus. Processor 20 may be configured to control the functioning of the transmitter and receiver by effecting control signaling via electrical leads to the transmitter and receiver. Likewise, processor 20 may be configured to control other elements of apparatus 10 by effecting control signaling via electrical leads connecting processor 20 to the other elements, such as a display or a memory. The processor 20 may, for example, be embodied in a variety of ways including circuitry, at least one processing core, one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits (for example, an application specific integrated circuit (ASIC), a field programmable gate array (FPGA), and/or the like), or some combination thereof. Accordingly, although illustrated in FIG. 7 as a single processor, in some example embodiments the processor 20 may comprise a plurality of processors or processing cores.

Signals sent and received by the processor 20 may include signaling information in accordance with an air interface standard of an applicable cellular system, and/or any number of different wireline or wireless networking techniques, comprising but not limited to Wi-Fi, wireless local access network (WLAN) techniques, such as Institute of Electrical and Electronics Engineers (IEEE) 802.11, 802.16, and/or the like. In addition, these signals may include speech data, user generated data, user requested data, and/or the like.

In some example embodiments, the apparatus 10 may be capable of operating with one or more air interface standards, communication protocols, modulation types, access types, and/or the like. For example, the apparatus 10 and/or a cellular modem therein may be capable of operating in accordance with various first generation (1G) communication protocols, second generation (2G or 2.5G) communication protocols, third-generation (3G) communication protocols, fourth-generation (4G) communication protocols, Internet Protocol Multimedia Subsystem (IMS) communication protocols (for example, session initiation protocol (SIP) and/or the like. For example, the apparatus 10 may be capable of operating in accordance with 2G wireless communication protocols IS-136, Time Division Multiple Access TDMA, Global System for Mobile communications, GSM, IS-95, Code Division Multiple Access, CDMA, and/ or the like. In addition, for example, the apparatus 10 may be capable of operating in accordance with 2.5G wireless communication protocols General Packet Radio Service (GPRS), Enhanced Data GSM Environment (EDGE), and/or the like. Further, for example, the apparatus 10 may be capable of operating in accordance with 3G wireless communication protocols, such as Universal Mobile Telecommunications System (UMTS), Code Division Multiple Access 2000 (CDMA2000), Wideband Code Division Multiple Access (WCDMA), Time Division-Synchronous Code Division Multiple Access (TD-SCDMA), and/or the like. The apparatus 10 may be additionally capable of operating in accordance with 3.9G wireless communication protocols, such as Long Term Evolution (LTE), Evolved Universal Terrestrial Radio Access Network (E-UTRAN), and/or the like. Additionally, for example, the apparatus 10 may be capable of operating in accordance with 4G wireless communication protocols, such as LTE Advanced, 5G, and/or the like as well as similar wireless communication protocols that may be subsequently developed.

It is understood that the processor 20 may include circuitry for implementing audio/video and logic functions of apparatus 10. For example, the processor 20 may comprise a digital signal processor device, a microprocessor device, an analog-to-digital converter, a digital-to-analog converter, and/or the like. Control and signal processing functions of the apparatus 10 may be allocated between these devices according to their respective capabilities. The processor 20 may additionally comprise an internal voice coder (VC) 20*a*, an internal data modem (DM) 20*b*, and/or the like. Further, the processor 20 may include functionality to operate one or more software programs, which may be stored in memory. In general, processor 20 and stored software instructions may be configured to cause apparatus 10 to perform actions. For example, processor 20 may be capable of operating a connectivity program, such as a web browser. The connectivity program may allow the apparatus 10 to transmit and receive web content, such as location-based content, according to a protocol, such as wireless application protocol, WAP, hypertext transfer protocol, HTTP, and/or the like.

In some example embodiments, apparatus 10 may also comprise a user interface including, for example, an earphone or speaker 24, a ringer 22, a microphone 26, a display 28, a user input interface, and/or the like, which may be operationally coupled to the processor 20. The display 28 may, as noted above, include a touch sensitive display, where a user may touch and/or gesture to make selections, enter values, and/or the like. The processor 20 may also include user interface circuitry configured to control at least some functions of one or more elements of the user interface, such as the speaker 24, the ringer 22, the microphone 26, the display 28, and/or the like. The processor 20 and/or user interface circuitry comprising the processor 20 may be configured to control one or more functions of one or more elements of the user interface through computer program instructions, for example, software and/or firmware, stored on a memory accessible to the processor 20, for example, volatile memory 40, non-volatile memory 42, and/or the like. The apparatus 10 may include a battery for powering various circuits related to the mobile terminal, for example, a circuit to provide mechanical vibration as a detectable output. The user input interface may comprise devices allowing the apparatus 20 to receive data, such as a keypad 30 (which can be a virtual keyboard presented on display 28 or an externally coupled keyboard) and/or other input devices.

As shown in FIG. 7, apparatus 10 may also include one or more mechanisms for sharing and/or obtaining data. For example, the apparatus 10 may include a short-range radio frequency (RF) transceiver and/or interrogator 64, so data may be shared with and/or obtained from electronic devices in accordance with RF techniques. To illustrate further, apparatus 10 may collect sensor data from sensors including heart rate monitor/sensor 101 as well as other devices. The apparatus 10 may include other short-range transceivers, such as an infrared (IR) transceiver 66, a Bluetooth™ (BT) transceiver 68 operating using Bluetooth™ wireless technology, a wireless universal serial bus (USB) transceiver 70, a Bluetooth™ Low Energy transceiver, a ZigBee transceiver, an ANT transceiver, a cellular device-to-device transceiver, a wireless local area link transceiver, and/or any other short-range radio technology. Apparatus 10 and, in particular, the short-range transceiver may be capable of transmitting data to and/or receiving data from electronic devices within the proximity of the apparatus, such as within 10 meters, for example. The apparatus 10 including the Wi-Fi or wireless local area networking modem may also be capable of transmitting and/or receiving data from electronic devices according to various wireless networking techniques, including 6LoWpan, Wi-Fi, Wi-Fi low power, WLAN techniques such as IEEE 802.11 techniques, IEEE 802.15 techniques, IEEE 802.16 techniques, and/or the like.

The apparatus 10 may comprise memory, such as a subscriber identity module (SIM) 38, a removable user identity module (R-UIM), an eUICC, an UICC, and/or the like, which may store information elements related to a mobile subscriber. In addition to the SIM, the apparatus 10 may include other removable and/or fixed memory. The apparatus 10 may include volatile memory 40 and/or non-volatile memory 42. For example, volatile memory 40 may include Random Access Memory (RAM) including dynamic and/or static RAM, on-chip or off-chip cache memory, and/or the like. Non-volatile memory 42, which may be embedded and/or removable, may include, for example, read-only memory, flash memory, magnetic storage devices, for example, hard disks, floppy disk drives, magnetic tape, optical disc drives and/or media, non-volatile random access memory (NVRAM), and/or the like. Like volatile memory 40, non-volatile memory 42 may include a cache area for temporary storage of data. At least part of the volatile and/or non-volatile memory may be embedded in processor 20. The memories may store one or more software programs, instructions, pieces of information, data, and/or the like which may be used by the apparatus for performing operations disclosed herein. The memories may comprise an identifier, such as an international mobile equipment identification (IMEI) code, capable of uniquely identifying apparatus 10. The memories may comprise an identifier, such as an international mobile equipment identification (IMEI) code, capable of uniquely identifying apparatus 10. In the example embodiment, the processor 20 may be configured using computer code stored at memory 40 and/or 42 to control and/or provide one or more aspects disclosed herein (see, for example, processes 300-600).

Some of the embodiments disclosed herein may be implemented in software, hardware, application logic, or a combination of software, hardware, and application logic. The software, application logic, and/or hardware may reside on memory 40, the control apparatus 20, or electronic components, for example. In some example embodiment, the application logic, software or an instruction set is maintained on any one of various conventional computer-readable media. In the context of this document, a "computer-readable medium" may be any non-transitory media that can contain, store, communicate, propagate or transport the instructions for use by or in connection with an instruction execution system, apparatus, or device, such as a computer or data processor circuitry, with examples depicted at FIG. 7, computer-readable medium may comprise a non-transitory computer-readable storage medium that may be any media that can contain or store the instructions for use by or in connection with an instruction execution system, apparatus, or device, such as a computer.

Without in any way limiting the scope, interpretation, or application of the claims appearing below, a technical effect of one or more of the example embodiments disclosed herein is way to provide a more reliable/accurate indication of heart rate in the form of a MHR. Without in any way limiting the scope, interpretation, or application of the claims appearing below, a technical effect of one or more of the example embodiments disclosed herein is way to provide a more reliable/accurate analysis of noisy sensor data from a sensor that is prone to data errors, for example a wrist attached sensor.

Although some of the examples refer to determining a minimum heart rate value, the subject matter disclosed herein may be used to determine a low or minima for other types of data collected from a subject, such as blood pressure, insulin level/blood sugar, cholesterol level, respiration rate, and/or the like. Moreover, the processing used to determine a low or minima may also process implemented to robustly estimate the minimum of any sensor signal or time-series measurements in domains outside of biology such as industrial process values and/or the like.

The subject matter described herein may be embodied in systems, apparatus, methods, and/or articles depending on the desired configuration. For example, the base stations and user equipment (or one or more components therein) and/or the processes described herein can be implemented using one or more of the following: a processor executing program code, an application-specific integrated circuit (ASIC), a digital signal processor (DSP), an embedded processor, a field programmable gate array (FPGA), and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device. These computer programs (also known as programs, software, software applications, applications, components, program code, or code) include machine instructions for a programmable processor, and may be implemented in a high-level procedural and/or object-oriented programming language, and/or in assembly/machine language. As used herein, the term "computer-readable medium" refers to any computer program product, machine-readable medium, computer-readable storage medium, apparatus and/or device (for example, magnetic discs, optical disks, memory, Programmable Logic Devices (PLDs)) used to provide machine instructions and/or data to a programmable processor, including a machine-readable medium that receives machine instructions. Similarly, systems are also described herein that may include a processor and a memory coupled to the processor. The memory may include one or more programs that cause the processor to perform one or more of the operations described herein.

Although a few variations have been described in detail above, other modifications or additions are possible. In particular, further features and/or variations may be provided in addition to those set forth herein. Moreover, the implementations described above may be directed to various combinations and subcombinations of the disclosed features and/or combinations and subcombinations of several further features disclosed above. Other embodiments may be within the scope of the following claims.

If desired, the different functions discussed herein may be performed in a different order and/or concurrently with each other. Furthermore, if desired, one or more of the above-described functions may be optional or may be combined. Although various aspects of some of the embodiments are set out in the independent claims, other aspects of some of the embodiments comprise other combinations of features from the described embodiments and/or the dependent claims with the features of the independent claims, and not solely the combinations explicitly set out in the claims. It is also noted herein that while the above describes example embodiments, these descriptions should not be viewed in a limiting sense. Rather, there are several variations and modifications that may be made without departing from the scope of some of the embodiments as defined in the appended claims. Other embodiments may be within the scope of the following claims. The term "based on" includes "based on at least." The use of the phase "such as" means "such as for example" unless otherwise indicated.

What is claimed is:

1. An apparatus comprising:
   at least one processor; and
   at least one memory including program code which when executed configures the apparatus to at least:
   receive, from at least one heart rate sensor, a heart rate data set collected from a subject over at least one session;
   filter the heart rate data set to remove at least one heart rate value failing to satisfy a predetermined time duration threshold defining one or more patches of values within the heart rate data set;
   generate, from the filtered heart rate data set, a histogram;
   adapt a percentile range of the histogram to further filter the filtered heart rate data set included in the generated histogram to generate the one or more patches of values within the heart rate data set that satisfy the predetermined time duration threshold;
   determine, for the one or more patches, one or more respective minimum heart rate values;
   determine, based on the one or more respective minimum heart rate values, one or more respective candidate minimum heart rates;
   determine, based on the determined one ore more respective candidate minimum heart rate, a final minimum heart rate; and
   provide the final minimum heart rate.

2. The apparatus of claim 1, wherein the heart rate data set includes heart rate data associated with a sleep session of the subject.

3. The apparatus of claim 1, wherein the adapted percentile range comprises an adaptive threshold to filter the histogram of the heart rate data set.

4. The apparatus of claim 3, wherein at least one heart rate data value is removed from the heart rate data set by applying the adaptive threshold.

5. The apparatus of claim 1, wherein the apparatus is further configured to at least segment the heart rate data set into a plurality of patches.

6. The apparatus of claim 5, wherein the apparatus is further configured to at least remove a patch when the patch is less than the predetermined time duration threshold.

7. The apparatus of claim 1, wherein the final minimum heart rate is determined over a plurality of sessions.

8. The apparatus of claim 7, wherein the final minimum heart rate is determined as a minimum having a threshold amount of repeat values within the histogram.

9. The apparatus of claim 1, wherein the heart rate data set includes awake state heart rate data.

10. The apparatus of claim 9, wherein the apparatus is further configured to at least estimate, from the awake state heart rate data, sleep state heart rate data.

11. The apparatus of claim 9, wherein the apparatus is further configured to at least determine the one or more respective minimum heart rates based at least in part on the sleep state heart rate data estimated from the awake state heart rate data.

12. The apparatus of claim 1, wherein the apparatus comprises a server coupled to an internet.

13. The apparatus of claim 1, wherein the apparatus comprises a user equipment.

14. The apparatus of claim 1, wherein the at least one heart rate sensor wirelessly couples to the apparatus.

15. The apparatus of claim 1, wherein the final minimum heart rate is provided in response to a query for the one or more respective minimum heart rate value.

16. A method comprising
receiving, from at least one heart rate sensor, a heart rate data set collected from a subject over at least one session;
filtering the heart rate data set to remove at least one heart rate value failing to satisfy a predetermined time duration threshold defining one or more patch of values within the heart rate data set;
generating, from the filtered heart rate data set, a histogram;
adapting a percentile range of the histogram to further filter the filtered heart rate data set included in the generated histogram to generate the one or more patches of values within the heart rate data set that satisfy the predetermined time duration threshold;
determining, for the one or more patches, one or more respective minimum heart rate values;
determining, based on the one or more respective minimum heart rate values, one or more respective candidate minimum heart rates;
determining, based on the determined one or more respective candidate minimum heart rate, a final minimum heart rate; and
providing the final minimum heart rate.

17. The method of claim 16, wherein the heart rate data set includes heart rate data associated with a sleep session of the subject.

* * * * *